United States Patent [19]

Crawford, Jr. et al.

[11] 4,267,276

[45] May 12, 1981

[54] MEDICAL SPECIMEN CULTURE BOTTLE

[75] Inventors: Andrew B. Crawford, Jr.; Gerald J. Wade, both of Littleton, Colo.

[73] Assignee: Honeywell Inc., Minneapolis, Minn.

[21] Appl. No.: 79,696

[22] Filed: Sep. 28, 1979

[51] Int. Cl.³ .............................................. C12M 1/34
[52] U.S. Cl. ................... 435/291; 204/195 B; 204/242; 204/1 T; 435/296; 435/299
[58] Field of Search .................. 204/195 B, 1 E, 242; 435/291, 287, 296, 299, 817

[56] References Cited

U.S. PATENT DOCUMENTS

| | | | |
|---|---|---|---|
| 3,449,210 | 6/1969 | Rohde | 435/296 |
| 3,743,581 | 7/1973 | Cady et al. | 435/291 X |
| 3,870,602 | 3/1975 | Froman et al. | 435/296 |
| 3,890,201 | 6/1975 | Cady | 435/291 |
| 3,938,035 | 2/1976 | Fletcher et al. | 204/195 R |
| 4,121,976 | 10/1978 | Gleeson | 435/296 X |

Primary Examiner—Robert J. Warden
Attorney, Agent, or Firm—Laurence J. Marhoefer; Lockwood D. Burton; Mitchell J. Halista

[57] ABSTRACT

A micro-organism culture bottle is molded of a high strength, high transparency, high temperature plastic which exhibits low permeability to oxygen and carbon dioxide and which is chemically inert to the substances intended to be used therewith. The neck of the bottle is asymmetrically positioned on the front face of the bottle to be located below the liquid level line when the bottle is operational to permit an in situ subculture extraction. A pair of substantially identical electrodes are supported from the rear wall of the bottle and extend parallel to the bottom of the bottle in a position to be also totally below the liquid level line. A frosted area on the front face of the bottle is provided upon which pertinent data may be written.

11 Claims, 3 Drawing Figures

U.S. Patent  May 12, 1981  4,267,276
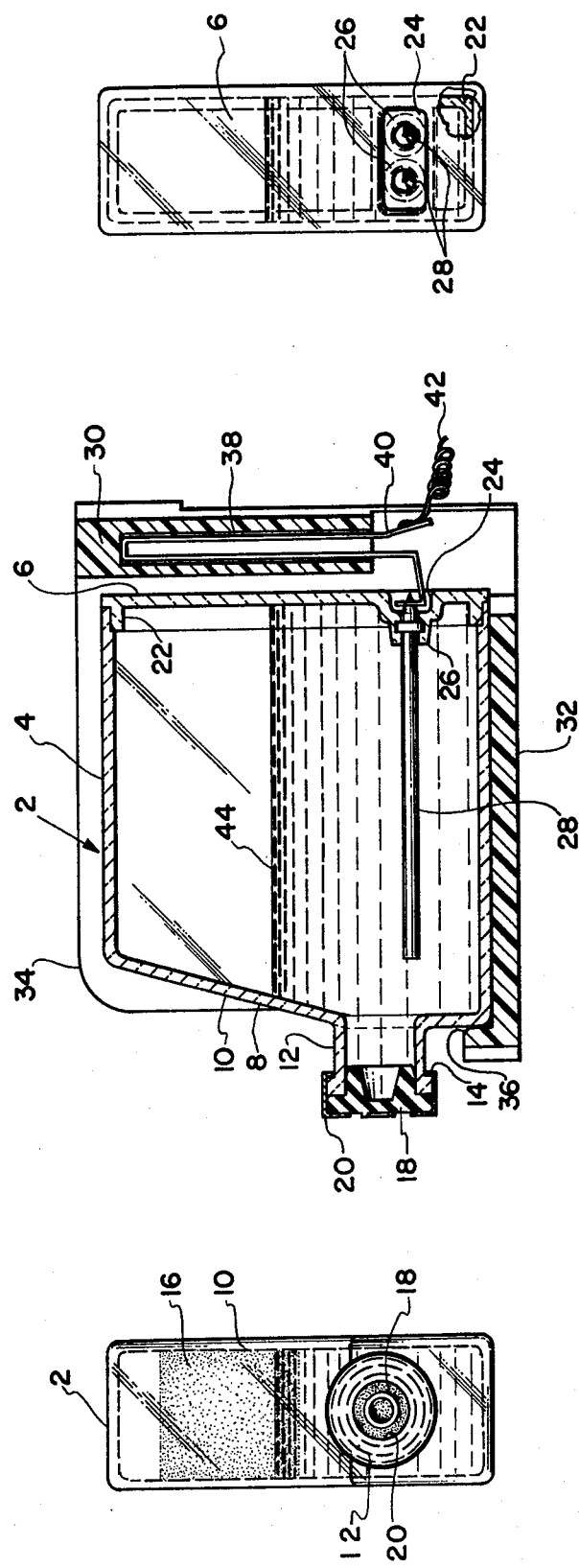
F I G. 3
F I G. 1
F I G. 2

MEDICAL SPECIMEN CULTURE BOTTLE

BACKGROUND OF THE INVENTION

The present invention relates to medical diagnostic apparatus. More particularly, it relates to a medical specimen culture bottle.

In the field of medical diagnostics, various conditions of a patient have been identified by the preparation of a blood sample in a culture medium, incubating the mixture, then determining presence and the growth rate of micro-organisms in the culture sample. A number of different arrangements have been made in an effort to provide an efficient, accurate, reliable and repeatable environment for the determination of bacterial growth. None have been entirely satisfactory. Many have not provided the capability of close control over the gas and liquid content of the culture bottle. None have provided a capability for the extraction of a subculture sample without removal of the bottle from the incubator-measuring apparatus. Few are sufficiently inexpensive to be disposable after a single use.

SUMMARY OF THE INVENTION

It is, accordingly, an object of the present invention to provide an improved medical specimen culture bottle which obviates the shortcomings of previous apparatus.

It is another object of the present invention to provide an improved culture bottle which provides capability of close control over the content thereof, which provides an efficient accurate and reliable apparatus for the determination of bacterial growth.

In accomplishing these and other objects, there has been provided, in accordance with the present invention, an improved culture bottle molded from a tough high temperature thermoplastic which is characterized in clear transparency which is chemically inert to the substances with which it is intended to be used and is relatively impermeable to oxygen and carbon dioxide. The bottle is molded in two pieces, a main body and a base portion which are subsequently bonded together. The base portion carries a pair of electrodes which are designed to extend a substantial distance into the main body of the bottle and to be totally submerged in the liquid contents of the bottle when the bottle is placed in operative position. The bottle is provided with a neck member extending from the face opposite the base portion and offset with respect to the center line of the bottle whereby said neck member is also below the level of the liquid content of the bottle when the bottle is in operative position. The neck is plugged by a live rubber stopper through which an inoculum may be injected and through which subculture samples may be extracted.

BRIEF DESCRIPTION OF THE DRAWINGS

A better understanding of the present invention may be had from the following detailed description when read in the light of the accompanying drawings, in which:

FIG. 1 is a side elevation view of a bottle in cross-section, embodying the present invention;

FIG. 2 is a front view of the bottle shown in FIG. 1; and

FIG. 3 is a rear view of the bottle shown in FIG. 1.

DETAILED DESCRIPTION

Referring now to the drawings in more detail, there is shown a culture bottle 2 having a main body portion 4 and a base portion 6. These two portions of the bottle are molded as by injection molding techniques, from high strength, high temperature, clear plastic molding resins. One molding resin that has exhibited satisfactory characteristics and is preferred in the present application is polymethylpentene (TPX). Another plastic material which has proven satisfactory is polyvinylsulfone. Another but less desirable plastic material is polycarbonate. Among the characteristics of these plastics are (1) they have a relatively high melting temperature (the polymethylpentene has a vicat function about 178° C. The others have a vicat function above 150° C.). Thus these materials exhibit a mechanical stability at temperatures up to and including 150° C. (2) they exhibit a high clear transparency to light, (3) they exhibit a low permeability to oxygen and carbon dioxide, (4) they are chemically inert to the substances with which they will be used; they will neither be dissolved by nor enter into combination with those substances, and (5) they are relatively light in weight yet mechanically strong. The bottle is designed to be substantially rectangular in all planes with the exception that the surface, which will be referred to as the front surface, is truncated to provide a portion of the surface which is sloping. In a bottle constructed in accordance with the present invention, the bottle was approximately 75 millimeters long, 70 millimeters high and 25 millimeters wide and is designed to have an internal volume of approximately 100 cubic centimeters.

A neck 12 is provided for the bottle extending outwardly from the front surface 8 of the bottle 2. On the outer end of the neck 12 there is formed a radially outward extending lip 14. The sloping portion 10 of the front surface 8 has a major part of its surface 16 frosted. The frosted surface 16 provides a surface where upon identifying data relative to the patient may be written. The sloping surface 10 which, in the exemplary embodiment, slopes at an angle approximately 15° from the vertical, provides an improved viewing angle for the operator (or apparatus involving bottles of the type herein described) to easily read the data recorded on the frosted surface 16. The neck 12 is offset from the centerline of the bottle and is approximately centered on the lower half of the front face 8 of the bottle 2. The open neck of the bottle is plugged by a rubber stopper 18. The stopper 18 seals the open neck of the bottle against contamination and is held in place by a thin metal annulus 20 which overlies a portion of the outer surface of the stopper 18 and is crimped under the lip 14 of the neck 12.

The opposite end of the main body 4 of the bottle 2 is formed as an open end. The base portion 6 of the bottle 2 is formed to fit closely into the open end of the main body portion 4 and may be sealed thereto by means of ultrasonic welding, for example. The base portion 6 is molded with a basically external flat surface and formed with an inwardly extending lip 22 which is dimensioned to fit within the open end of the main body portion 4 of the bottle 2. It is this lip 22 which is effectively bonded to the main body portion as hereinbefore set forth.

The base portion 6 has formed therein a recess 24, the recess being located near the lower end of the base portion 6. On the inner surface, that is, inwardly of the bottle, of the base portion 6 there is a first and second boss 26 projecting inwardly of the bottle from the inner surface of the recessed portion of the base member 6. A metallic electrode 28 is sealed into and through each of the two bosses 26 and extends parallel to each other and to the inside walls of the main body portion 4 of the bottle 2. These electrodes are preferably made of surgical stainless steel. In a preferred embodiment, the electrodes 28 extend through the bosses 26 and the end wall of the recess 24 and terminate in a conical end which extends into the recess 24 but does not extend beyond the basic flat surface of the outer surface of the base portion 6. Again, in a preferred arrangement, the electrodes 28 are sealed into the base portion 6 prior to the assembly of the base portion 6 with the main body portion 4. With such an arrangement, after the electrodes are sealed in position which may, again, be accomplished through ultrasonic welding techniques, the electrodes may be surface treated before the base is sealed to the main body of the bottle.

After the base has been sealed to the main body 4, the bottle may be partially filled, about half full, with a nutrient medium with the remainder of the space filled with a predetermined mixture of gases. The filling process is preferably accomplished in a controlled atmosphere as taught in the aforementioned copending application of Robert C. Wohr. While the bottle is in the controlled atmosphere, the rubber stopper 18 is inserted in the neck of the bottle and the metallic annulus 20 is crimped over the lip 14 to permanently seal the bottle and its contents. The bottles thus prepared and sealed may then be transported to a suitable clinic or laboratory to await use. When it is desired to put the bottle into use, a sample of the patients blood or another desired inoculum is injected into the interior of the bottle as by a hypodermic type syringe through the thinner portion of the rubber stopper 18. The withdrawal of the syringe needle provides a minimal disturbance of the hermetic seal of the bottle. The bottle thus prepared would then be placed in a suitable incubator environment where the bottle and its contents may be subjected to a suitable temperature and agitation to promote the rapid growth of micro-organisms in the culture medium.

In accordance with the present invention, it is anticipated that the incubator apparatus will include a receptacle into which the bottle 2 may be inserted. Such a receptacle is illustrated in cross-section form in FIG. 1. The receptacle includes a back wall member 30 and a bottom wall member 32. The receptacle structure may be in the form of a carousel with periodic separator panels 34 to define individual receptacle spaces. The bottom wall member 32 is provided with a recess to define a lip or shoulder 36 at the forward edge of the bottom wall member 32.

The back wall member 30 has a recess 38 formed therein to retain a spring/electrical contact member 40. The spring/contact member 40 is formed basically in a hairpin shape with one of the legs formed to establish a spring contact engagement with a corresponding one of the conical external ends of the electrodes 28. The other end of the spring/contact member 40 is positioned to receive an electrical lead connection 42 which may be secured to the end of the spring/contact member 40 as by conventional wire wrap techniques. It is, of course, anticipated that the receptacle structure will be enclosed in a suitable housing to provide the thermal environment desired. Access to the individual receptacles will be gained through suitable door members in the housing. Since such housing and door members form no part of the present invention they are not illustrated herein.

The receptacle structure is illustrated herein to show the positioning of the culture bottle when it is in operational position. When the bottle has been filled and sealed as hereinbefore mentioned and injected with the selected inoculum, the bottle is placed in the receptacle in the position shown in FIG. 1 with the side wall of the bottle adjacent and parallel to the two electrodes being at the bottom. In this position, the conical external ends of the electrodes 28 engage the spring/contacts 40. The engagement with the spring contacts 40 serves two purposes. First, it establishes electrical contact with the electrodes 28. Second, the spring action of the member 40 biases the bottle into a forward movement to be firmly held in place by the engagement of the front face 8 of the bottle 2 with the shoulder 36 at the forward end of the bottom wall 32 of the receptacle. The electrical leads 42 are connected to suitable electronic measuring circuitry to obtain signals representative of the growth of the micro-organisms in the culture.

As was previously mentioned, the neck 12 of the bottle 2 is located asymmetrically with respect to the main body of the bottle and is specifically positioned approximately centrally of the lower half of the bottle, referenced to the operational position as illustrated in the drawings. The neck of the bottle serves a multiplicity of functions. Not only does it provide means for admitting the nutrient fluid and the controlled mixture of gases into the bottle during a filling operation, but when the bottle is thus filled and sealed, the neck provides a convenient handle for inserting the bottle into and removing the bottle from the incubator receptacle. When in the course of evaluating the activity of the substances within the bottle it is desired to extract a sample of those substances for an external subculture, such a sample may be extracted from the bottle by a hypodermic type syringe with the needle being inserted through the inner portion of the rubber stopper 18. With the neck of the bottle eccentrically located in the lower half of the front surface of the bottle, the neck lies entirely below the liquid level 44 of the active culture medium. In this position, the insertion of the syringe needle through the stopper is always in the active medium, requiring no tilting movement of the bottle in order to facilitate the extraction of such a sample. Thus, the subculture sample may be extracted from the bottle without removing the bottle from the incubator atmosphere. The elimination of the need for removing the bottle from the incubator thereby eliminates an undesirable interruption to the incubation process and further eliminates a potential confusion if the bottle is inadvertently either not returned to the incubator or returned to the wrong slot in the incubator.

It is also to be noted that, with the bottle in the operational position as illustrated in the figures, the two electrodes are totally submerged beneath the liquid level 44. It has been found that if the electrodes extend in a position or direction to be partially submerged in the liquid and partially exposed to the gases above the liquid, that a so called tri-junction exists which tends to produce an unstable artifact into the resulting electrical signal. Such an artifact would therefore cause the analysis of the activity in the fluid to be significantly unreliable. Further, the positioning of the electrodes is such that they will remain totally submerged while the contents of the bottle are being agitated. In accordance with the present invention it has been found that when the electrodes 28 are substantially identical in structure and dimension and are spaced from and parallel to each other as well as to the adjacent sidewalls and bottom of the bottle 2, that a highly reliable, repeatable signal is obtained indicative of the growth activity, or lack of same, of the microorganism culture in the medium. The spacing of the electrodes 28 from the bottom of the bottle, but parallel thereto, maintains those electrodes in a position to be free from contamination by any substance that may tend to precipitate out of the solution. Red blood cells, for example, tend to collect at the bottom of the bottle and would produce an erroneous reading if they were allowed to contaminate the electrodes.

The bottle constructed and prepared in accordance with the present invention is sufficiently inexpensive that the bottles may be considered as a single use disposable item.

Thus, there has provided, in accordance with the present invention, an improved medical specimen culture bottle which provides the capability of close control over the gas and liquid content of the culture bottle, which provide for the capability for the extraction of a sub-culture sample without the removal of the bottle from the incubator-measuring apparatus, which is sufficiently inexpensive to be disposable after a single use, which is light in weight yet mechanically tough and which provides an environment for an efficient, accurate and reliable determination of the growth rate of culture samples.

The embodiments of the invention in which an exclusive property or privilege is claimed are defined as follows:

1. A micro-organism culture bottle comprising:
   a main body portion having five substantially rectangular surfaces and an open end,
   a base portion having a substantially rectangular planar surface, said base portion being dimensioned to fit and close said open end of said main body portion,
   said main body portion having a neck extending outwardly from the front face thereof opposite said open end, said neck being positioned asymmetrically positioned relative to said front surface, being located entirely within the lower half of said front surface;
   said base portion having recess form therein near one end of said base portion, and
   a pair of electrode rods sealed through said base portion and having an external tip extending into but not beyond said recess,
   said base portion being bonded into sealing relation to said open end of said main body portion with said electrode rods extending into said main body portion spaced from and parallel to each other and the adjacent walls of said main body portion,
   said neck and said electrodes being positioned to be below the liquid content of the bottle when said bottle is sealed and prepared for operation.

2. A micro-organism culture bottle as set forth in claim 1 wherein said main body portion and said base portion are molded from a plastic material characterized as transparent, impermeable to oxygen and carbon dioxide and mechanically stable at temperatures up to and including 150° C.

3. A micro-organism culture bottle as set forth in claim 2 wherein said plastic material is chosen from the group including polymethylpentene, polyvinylsulfone and polycarbonate.

4. A micro-organism culture bottle as set forth in claim 3 wherein said plastic material is polymethylpentene.

5. A micro-organism culture bottle as set forth in claim 3 wherein said plastic material is polyvinylsulfone.

6. A micro-organism culture bottle as set forth in claim 3 wherein said plastic material is polycarbonate.

7. A micro-organism culture bottle as set forth in claim 3 wherein said base portion is bonded and hermetically sealed to said main body portion by ultrasonic welding.

8. A micro-organism culture bottle as set forth in claim 3 wherein the upper portion of said front face of said bottle is provided with a frosted surface whereupon pertinent data may be written.

9. A micro-organism culture bottle as set forth in claim 8 wherein said upper portion of said front face of said bottle slopes backward toward said base portion to provide an improved angle for reading data written on said frosted surface.

10. A micro-organism culture bottle as set forth in claim 2 wherein said electrode rods are substantially indentical in composition and dimension.

11. A micro-organism culture bottle as set forth in claim 10 wherein said electrode rods are made of surgical stainless steel.

* * * * *